US006179937B1

(12) United States Patent
Leveritt et al.

(10) Patent No.: US 6,179,937 B1
(45) Date of Patent: Jan. 30, 2001

(54) STABILIZERS FOR HYDROXYLAMMONIUM NITRATE, HYDROXYLAMMONIUM NITRATE DERIVATIVES, HYDROXYLAMINE AND COMPOSITIONS CONTAINING THE SAME

(75) Inventors: Chares S. Leveritt, Jarrettsville; Steven W. Bunte, Baltimore, both of MD (US); Eugene F. Rothgery, N. Branford; Carl G. Seefried, Southbury, both of CT (US); Nathan Klein, Baltimore, MD (US)

(73) Assignee: The United States of America as represented by the Secretary of the Army, Washington, DC (US)

( * ) Notice: Under 35 U.S.C. 154(b), the term of this patent shall be extended for 0 days.

(21) Appl. No.: 09/168,330

(22) Filed: Oct. 1, 1998

Related U.S. Application Data (60) Provisional application No. 60/064,000, filed on Oct. 15, 1997.

(51) Int. Cl.[7] ............................ C06B 31/00; C06B 31/02; C07F 9/58; C07F 9/28; C07F 5/02
(52) U.S. Cl. .................................. 149/45; 546/3; 546/13; 546/22
(58) Field of Search ................... 546/3, 13, 22; 149/92, 45

(56) References Cited

U.S. PATENT DOCUMENTS

| 3,145,082 | 8/1964 | Rausch et al. ................. 423/275 |
| 5,258,104 | 11/1993 | Crawlfield et al. ............ 204/91 |
| 5,510,097 | 4/1996 | Crawlfield et al. ............ 423/387 |
| 5,703,323 | 12/1997 | Rothgery et al. ............ 149/88 |

OTHER PUBLICATIONS

Hansen, R., et al., "Processes for Assessing the Thermal Stability of HAN–Based Liquid Propellants, Final Report," BRL–CR–635, Ballistic Research Laboratory, Aberdeen Proving Ground, Maryland (Jul., 1990).

*Primary Examiner*—Alan L. Rotman
(74) *Attorney, Agent, or Firm*—Paul S. Clohan, Jr.; Mark D. Kelly (57) ABSTRACT

The stability of HAN, HAN derivatives or hydroxylamine, and compositions comprising these is considerably enhanced by employing a stabilizing effective amount of a stabilizer selected from (a) a pyridine or pyridone salt, or an acid thereof; (b) a diphosphonate or methylenephosphonate salt, or an acid thereof; or (c) a mixture of two or more stabilizers, wherein at least one is selected from (a) and at least one is selected from (b). Stabilized HAN, HAN derivatives, or hydroxylamine or compositions comprising HAN, an HAN derivative or hydroxylamine, along with a process for providing these stabilized compositions is described. A stabilizer mixture having enhanced, synergistic stabilizing properties is described as well.

61 Claims, 4 Drawing Sheets

Effect of Additives on LP XM46
50 ppm Fe, 0.1% Stabilizer, @ 65°C

Figure 4 ately 0.0001% wt. to 2% wt.
STABILIZERS FOR HYDROXYLAMMONIUM NITRATE, HYDROXYLAMMONIUM NITRATE DERIVATIVES, HYDROXYLAMINE AND COMPOSITIONS CONTAINING THE SAME

RELATED APPLICATION

This application claims the benefit of U.S. Provisional Application No. 60/064,000, filed Oct. 15, 1997.

GOVERNMENT INTEREST

The invention described herein may be manufactured, used and licensed by or for the U.S. Government without payment to us of any royalty thereon.

FIELD OF THE INVENTION

The present invention relates to stabilizers for hydroxylammonium nitrate (HAN), HAN derivatives, and their precursor, hydroxylamine and compositions comprising HAN, an HAN derivative or hydroxylamine. The present invention further relates to stabilized HAN, HAN derivatives and hydroxylamine, as well as stabilized compositions containing HAN, an HAN derivative or hydroxylamine. HAN, HAN derivatives or hydroxylamine and compositions comprising HAN, an HAN derivative or hydroxylamine are stabilized against decomposition by the addition of a stabilizing effective amount of a stabilizer(s) within the scope of the present invention. More specifically, the present invention relates to stabilized compositions, such as liquid propellants (also referred to herein as "LP") that contain HAN, an HAN derivative or hydroxylamine and a fuel. HAN derivatives referred to within the scope of the present invention are compounds prepared by substituting a functional group on the amine in place of a hydrogen ion—i.e. diethylhydroxylammonium nitrate.

BACKGROUND OF THE INVENTION

HAN, HAN derivatives and hydroxylamine are useful oxidizers in various propellant formulations such as, for example, those used for guns, rockets, satellites, gas generators, and the like. HAN, specifically, is an oxidizer for propellants that has recently become available in commercial quantities. Processes for preparing HAN are set forth in U.S. Pat. Nos. 5,510,097 and 5,258,104. HAN, its derivatives and hydroxylamine have many desirable properties, such as high oxygen content, high water solubility as well as containing no halogen atoms. Unfortunately, the storage stability for HAN, HAN derivatives or hydroxylamine, and compositions containing them has been, and continues to be, a concern for which solutions are sought. The need exists to enhance the storage stability of HAN, HAN derivatives or hydroxylamine and compositions containing them.

Certain stabilizers for HAN, HAN derivatives and hydroxylamine are known. Some have been used to protect compositions containing HAN, HAN derivatives and hydroxylamine from unwanted degradation during storage prior to use. As disclosed in U.S. Pat. No. 3,145,082, chelating agents, such as the tetrasodium salt of ethylenediaminetetraacetic acid (EDTA) have been used as stabilizers for hydroxylamine. The prior art further teaches the use of aminophosphonic acids as stabilizers for HAN-based liquid propellant (LP) compositions. This is set forth in a technical report by R. Hansen et al., entitled "Processes for Assessing the Thermal Stability of HAN-Based Liquid Propellants, Final Report," BRL-CR-635, Ballistic Research Laboratory, Aberdeen Proving Ground, Md. (Jul., 1990).

There exists a continuing need to develop and provide means for which to provide enhanced stability to HAN, HAN derivatives and hydroxylamine, as well as for compositions comprising these. Being able to accomplish this in a cost-effective fashion is further desirable. The present invention provides a solution to meet the needs described.

BRIEF DESCRIPTION OF THE INVENTION

The present invention relates to stabilizers for HAN, HAN derivatives and hydroxylamine and compositions comprising these. The present invention further relates to stabilized HAN, HAN derivatives, or hydroxylamine-containing compositions comprising HAN, an HAN derivative or hydroxylamine and an effective stabilizing amount of a stabilizer within the scope of the present invention. The stabilizer is preferably present in said composition in an amount of between approximately 0.0001% wt. to 2% wt. based on the weight of said composition.

Stabilizers which may be employed herein are selected from (a) a pyridine or pyridone salt, or an acid thereof (Type I stabilizers); (b) a diphosphonate or methylenephosphonate salt, or an acid thereof (Type II stabilizers); or (c) a stabilizing mixture of at least one stabilizer selected from each of (a) and (b), above (Type III stabilizers). The stabilizers will be more specifically identified and defined in the detailed description of the invention.

Accordingly, it is an object of the present invention to provide stabilizers for HAN, HAN derivatives and hydroxylamine, and for compositions containing at least one of said HAN, HAN derivative or hydroxylamine.

It is another object of the present invention to provide a stabilized HAN, HAN derivative or hydroxylamine-containing composition comprising said HAN, HAN derivative or hydroxylamine and a stabilizing effective amount of a stabilizer ingredient to provide a storage-stable composition.

Yet a further object of the present invention is to provide a stabilized HAN, HAN derivative or hydroxylamine-containing composition comprising said HAN, HAN derivative or hydroxylamine and a stabilizer, wherein said stabilizer is present in said composition in an amount of between approximately 0.0001% wt. and 2% wt. based upon the weight of said composition.

It is a further object of the present invention to provide a process for stabilizing HAN, HAN derivatives or hydroxylamine against unwanted degradation during storage prior to use, which comprises contacting said HAN, HAN derivative, or hydroxylamine with a stabilizing effective amount of a stabilizer to provide a storage-stable composition.

Still a further object of the present invention is to provide a process for forming a storage-stable composition of HAN, an HAN derivative or hydroxylamine, or propellant formulations containing at least one of said HAN, HAN derivative or hydroxylamine, which comprises mixing a stabilizing effective amount of a stabilizer with a composition comprising HAN, an HAN derivative or hydroxylamine to provide said storage-stable composition.

It is a further object of the present invention to increase the shelf life of HAN, HAN derivatives, and hydroxylamine, and compositions comprising at least one of said ingredients.

The means to achieve these and other objectives of the present invention will be apparent from the following detailed description of the invention and claims.

BRIEF DESCRIPTION OF THE DRAWINGS

The present invention will be described with reference to the following figures.

DETAILED DESCRIPTION OF THE INVENTION

The stability of HAN, HAN derivatives or hydroxylamine, and compositions comprising these, has been found to be considerably enhanced by adding/mixing into said HAN, HAN derivative or hydroxylamine or composition comprising these, a stabilizing effective amount of a stabilizer selected from (a) a pyridine or pyridone salt, or an acid thereof (Type I stabilizer); (b) a diphosphonate or methylenephosphonate salt, or an acid thereof (Type II stabilizer); or (c) a mixture of two or more stabilizers, wherein at least one is selected from (a) and at least one is selected from (b), above (Type III stabilizer). These stabilizers are specifically described herein.

Compositions within which HAN, HAN derivatives or hydroxylamine are found include propellants. Sample propellant compositions which comprise these are set forth in Table 1. Among these propellants is LP XM46 (also known as LGP 1846), which is one of a new family of liquid gun propellants being developed by the U.S. Army.

TABLE 1

Composition of Liquid Propellant Mixtures and Gravimetric Impetus of Higher Energy LP Mixtures Compared to LP XM46 (LGP 1846)

| LGP | Chemical Composition (wt. %) | | | | Impetus (J/g) |
|---|---|---|---|---|---|
| | HAN | TEAN | DEHAN | Water | |
| 1846 | 60.8 | 19.2 | 0 | 20.0 | 900.8 |
| 1898 | 60.8 | 0 | 19.2 | 20.0 | — |
| 4640 | 60.8 | 11.5 | 7.7 | 20.0 | 923.7 |
| 4440 | 63.8 | 12.1 | 8.1 | 16.0 | 968.7 | wherein TEAN=triethanolammonium nitrate; and DEHAN=diethylhydroxylammonium nitrate (HAN derivative).

As already noted, storage stability is not only a problem for HAN, HAN derivatives and hydroxylamine, but it is also an issue for compositions containing them, such as propellants of the type described above. The storage stability issue can be demonstrated, for illustration purposes only, as follows: Hydroxylamine cations are present in a propellant composition comprising HAN. These cations are susceptible to, i.e., iron catalyzed decomposition. This decomposition results in the production of nitrogen oxides and nitric acid which causes the composition to become unstable. Due to this decomposition, the shelf life of the propellant composition is detrimentally affected. It is, therefore, desirable to control the generation of nitric acid or inhibit the formation of nitric acid in these compositions in order to improve their stability.

The present invention provides a solution to this problem, and provides for compositions comprising HAN, an HAN derivative and/or hydroxylamine, i.e. propellant compositions, having enhanced storage stability. The storage stability is enhanced by employing the stabilizers within the scope of the present invention. A process for producing such stabilized compositions is further described.

Ideally, all propellants, including those containing HAN, HAN derivatives and/or hydroxylamine, should have a shelf life of approximately 20 years. The present invention provides a means to achieve or exceed this shelf life goal.

(a) Pyridine or Pyridone Salt, or an Acid thereof as Stabilizers (Type I Stabilizers).

It has now been surprisingly found, in accordance with the present invention, that the stability against chemical degradation of HAN-, HAN derivative—and hydroxylamine-containing compositions is considerably enhanced by the incorporation into the compositions of a stabilizing effective amount of a select pyridine or pyridone stabilizer. Although numerous pyridine or pyridone type stabilizers within the scope of the present invention accomplish the stabilizing effect sought, the preferred pyridine or pyridone type stabilizer is the sodium salt of 2-hydroxypyridine-N-oxide ("NaHPNO"), which is commercially available. Without wishing to be bound by any particular theory, it is believed that the sodium ion in the stabilizer transchelates with soluble iron present in, or entering the HAN-, HAN derivative- or hydroxylamine-containing composition or propellant formulation from an outside source, to form a stable iron complex with the pyridine-N-oxide. As additional soluble iron enters the composition, for example from a storage container during storage and prior to use of the composition, additional formation of iron complex with the pyridine-N-oxide occurs.

The inventors have found that iron contaminated LP XM46, when treated with NaHPNO, exhibited a decomposition onset temperature significantly greater than that of pure LP XM46 as measured by Accelerated Rate Calorimetry (ARC). Note Example 1, below. This illustrates the significant stabilizing effect of the stabilizer additive to said HAN-containing propellant composition.

Other, pyridine or pyridone type stabilizers within the scope of the present invention include: 2-hydroxy4-methoxy-pyridine-N-oxide; 1,2-dimethyl-3-hydroxy-pyridine4-one; 4-methyl-pyridine-N-oxide; 6-methyl-pyridine-N-oxide; 1-methyl-3-hydroxypyridine-2-one; and combinations thereof. The stabilizers within the scope of the present invention may be employed in their acid form, or in their salt form, such as an alkali metal or alkaline earth metal salt, as well as salts made using Group IA metals, Group IIA metals and the transition metals, especially iron, nickel, chromium, copper and zinc. Other useful salt forms of these various stabilizers include the amine salts, lower alkylamine salts and alkanolamine salts.

Additional pyridine or pyridone type stabilizers within the scope of the present invention include zinc pyrithione, copper pyrithione, manganese pyrithione, nickel pyrithione, cobalt pyrithione, bismuth pyrithione, zirconium pyrithione, 1-hydroxy-6-substituted pyridones having a 6-position substituent selected from —O—R and —S—R, wherein R is a substituted or unsubstituted hydrocarbon radical having between 1 and 20 carbon atoms, and combinations thereof.

Representative structural formulas for various pyridine and pyridone stabilizers further within the scope of the present invention may be represented by the structural formulas set forth below as Formulas I, II and III.

(Formula I)

wherein X is a moiety selected from the group consisting of —SH, —OH, and —NH$_2$, n is an integer of 1 or 2, and R is hydrogen, a lower alkyl or a lower alkoxy group having from one to six carbon atoms;

(Formula II)

wherein R' is a moiety selected from the group consisting of hydrogen and a lower alkyl group having from one to six carbon atoms; and (Formula III)

wherein R" is a moiety selected from the group consisting of hydrogen and a lower alkyl group having from one to six carbon atoms, and R'" is a lower alkyl or lower alkoxy group having from one to six carbon atoms.

The pyridine or pyridone stabilizers within the scope of the present invention are to be employed into the composition to be stabilized in a stabilizing effective amount. They are suitably employed at a concentration range of approximately 0.0001% to 2% by weight of said composition. The preferred concentration level of the pyridine or pyridone stabilizer is 10 to 1000 parts per million (milligrams per kilogram) of the HAN-, HAN derivative- or hydroxylamine-containing composition to be stabilized.

(b) Diphosphonate or Methylenephosphonate Salt, or Acid thereof as Stabilizers (Type II Stabilizers).

Stability against chemical degradation of HAN-, HAN derivative- and hydroxylamine-containing compositions can also be accomplished within the scope of the present invention by employing into said compositions a stabilizing effective amount of a diphosphonate or methylenephosphonate salt, or an acid thereof as a stabilizer. Preferred stabilizers of this type include 1-hydroxyethylidene-1,1-diphosphonic acid and the corresponding tetrasodium salt thereof. These stabilizers are commercially available and are manufactured by Monsanto and marketed under the tradenames of Dequest 2010 and Dequest 2016D, respectively. Note Formula IV herein. Additional preferred stabilizers are hexamethylenediaminetetra(methylenephosphonic acid) and the corresponding hexapotassium salt, commercially available and manufactured by Monsanto, as well, and marketed under the tradenames Dequest 2051 and Dequest 2054, respectively. Note Formula V herein.

Diphosphonate or methylenephosphonate type stabilizers within the scope of the present invention also include: aminotri(methylenephosphonic acid) and its corresponding pentasodium salt, commercially available and manufactured by Monsanto and marketed under the tradenames Dequest 2000 and Dequest 2006, respectively (note Formula VI); diethylenetriaminepenta(methylenephosphonic acid) and its corresponding hexasodium salt, commercially available and manufactured by Monsanto and marketed under the tradenames Dequest 2060 and Dequest 2066, respectively (note Formula VI); and combinations thereof. These stabilizers may be employed in either their acid or salt form.

Phosphonic acids and their corresponding phosophonates are multifunctional metal ion control agents. They may be used as metal sequestrants, as deflocculants for resulting precipitates, and as surface coating or passive film on metal alloys having components with an affinity to phosphonates. By definition, phosphonic acids contain at least one —PO$_3$H$_2$ functional group attached to a carbon atom. When the above stabilizers are added to a propellant composition comprising HAN, an HAN derivative or hydroxylamine, for example, they form a chelate with any undesired contaminating metal ion, i.e. Fe, that may be present to form a water soluble complex. Metal ions may be present in the propellant composition from either the propellant composition itself or they may have been inadvertently introduced into the propellant by accident or contact with other materials.

The dispersive properties of diphosphonate or methylenephosphonate salts or acids make the agglomeration of growing crystals and other particulates more difficult. Diphosphonate or methylenephosphonate salts or acids thereof are strongly adsorbed onto surfaces, thus imparting repulsive charges and dispersion of solids. In addition to the ability of these stabilizers to deflocculate and disperse solids, they have the added characteristic of being able to maintain such systems in a dispersed state for an extended period of time because of their excellent hydrolytic stability.

The inventors have found that iron-contaminated LP XM46, when treated with a stabilizing effective amount of Dequest 2010, Dequest 2016D, Dequest 2051 or Dequest 2054, for instance, exhibited a decomposition rate that was significantly reduced from that of merely LP XM46 contaminated with iron as measured by titrimetric analysis of nitric acid buildup generated as the HAN in the LP XM46 decomposes.

Representative structural formulas for the various diphosphonate or methylenephosphonate salt or acid stabilizers within the scope of the present invention are set forth below as Formulas IV, V, VI and VII.

1-hydroxyethylidene-1,1-diphosphonic acid
(Dequest 2010)

(Formula IV)

and is corresponding tetrasodium salt (Dequest 2016D);

hexamethylenediaminetetra(methylenephosphonic acid) (Dequest 2051)

(Formula V)

and its corresponding hexapotassium salt (Dequest 2054);

aminotri(methylenephosphonic acid) (Dequest 2000)

(Formula VI)

and its corresponding pentasodium salt (Dequest 2006); and, diethylenetriaminepenta(methylenephosphonic acid) (Dequest 2060)

(Formula VII)

and its corresponding hexasodium salt (Dequest 2066).

These diphosphonate or methylenephosphonate type stabilizers are employed in the present invention at concentration levels of between approximately 0.0001% wt. to 2% wt. of the solution to be stabilized. The preferred concentration level of these stabilizers is between 10 to 3,000 parts per million (milligrams per kilogram) of the HAN-, HAN derivative- or hydroxylamine-containing composition to be stabilized.

(c) Combination of Pyridine or Pyridone Type Stabilizers (Type I) with Diphosphonate or Methylenephosphonate Type Stabilizers (Type II) Provide Enhanced Stabilizing Effect (=Type III Stabilizers).

It has been determined within the scope of the present invention that the stability of HAN, HAN derivatives and hydroxylamine and compositions containing HAN, an HAN derivative or hydroxylamine is more greatly enhanced by employing a stabilizer mixture (Type III stabilizer) comprising effective stabilizing amounts of (a) at least one pyridine and/or pyridone type stabilizer described above (Type I stabilizer), and (b) at least one diphosphonate or methylenephosphonate type stabilizer also described above (Type II stabilizer). Specific combinations, in specific proportions, of said Type I stabilizers and Type II stabilizers have been found to provide an unexpected, synergistic stabilizing effect when added to HAN, HAN derivatives and hydroxylamine or compositions comprising HAN, an HAN derivative or hydroxylamine.

As previously noted, controlling the generation of strong acid (i.e., nitric acid) in compositions comprising HAN, an HAN derivative or hydroxylamine improves the stability of these compositions. The alkali metal salts, for example, of both Type I and Type II stabilizers have been observed to act as weak bases in compositions comprising HAN, an HAN derivative or hydroxylamine. The presence of these stabilizers neutralizes excess strong acid which may be present in said compositions as a result of slow decomposition or due to the manufacturing process itself. If a stabilizing effective amount of these stabilizers, either individually or together, is employed, prolonged shelf life of the composition is observed. However, it has also been noted that if sufficient alkali metal salts, or combinations thereof, of these stabilizers are added to said compositions, an undesirable condition of apparent negative acidity may be produced, as determined by titrimetry. This condition of negative acidity is due to the liberation of free bases, such as hydroxylamine, triethanolamine or diethylhydroxylamine, depending on the initial composition of the HAN-, HAN derivative or hydroxylamine-containing composition (i.e., propellant). The negative acidity further leads to the decomposition of the far less stable free bases, such as hydroxylamine, and generation of $N_2O$ and $N_2$ gases in a quantity commensurate with the negative acidity content of the composition. In this negative acidity condition, the response of the HAN-, HAN derivative-, or hydroxylamine-containing propellant, for example, to the stimuli provided by Hazard Classification, Insensitive Munition and Vulnerability/ Survivability testing is seriously degraded. Accordingly, it is desirable to employ appropriate amounts of stabilizers such that a desirable, controlled level of acidity is attained.

It has been demonstrated that mixtures of Type I and Type II stabilizers can be formulated so that they can be used to control the initial acidity of these compositions to the desired level. Being able to control the initial acidity of said compositions translates to a composition having greater stability. Moreover, it has been determined and demonstrated that employing these types of stabilizer mixtures, in specific proportions, provide enhanced, synergistic, stabilizing effect to these compositions.

Using Type III stabilizers, one having ordinary skill in the art will be able to produce, for example, a propellant having an acid content, by specification, in the range of approximately 0% wt.<apparent acidity<0.05% wt. calculated as nitric acid. The lower apparent acidity level is selected to prevent the liberation of free amines, such as hydroxylamine, which are not very stable and decompose and provide serious problems when mechanical stimuli are applied. The upper apparent acidity level is selected to provide flexibility in attaining a propellant with desirable properties.

As set forth above, the undesirable property of negative acidity can result by employing excess Type I or Type II stabilizers into these propellant compositions. Any negative acidity may be countered by knowing the change in acidity produced by the single Type I or Type II stabilizer and then tailoring the initial propellant formulation to suit. For example, 0.1% wt. NaHPNO (Type I stabilizer) causes the apparent acidity of a tested propellant to move 0.045% wt. in the negative direction. Similarly, 0.2% wt. NaHPNO causes the apparent acidity to move 0.09% wt. in the negative direction. Accordingly, if a propellant composition contained 0.1% wt. NaHPNO, the manufacturer of the propellants would need to produce an initial propellant mixture having an apparent acidity of 0.045% wt. so that the final stabilized propellant composition employing NaHPNO would meet specification. If the propellant composition contained 0.2% wt. NaHPNO, the initial propellant mixture should be produced to have an apparent acidity of 0.09% wt. Employing the Type III stabilizers within the scope of the present invention, as can be seen in Example 3, provides a manufacturer of compositions comprising HAN, an HAN derivative or hydroxylamine (i.e., propellants) with a simple, very effective processing tool to control the apparent acidity of these compositions while at the same time provide enhanced stability to them. Use of the stabilizer herein provides a manufacturer with great flexibility in attaining a propellant, for example, with desirable properties.

The Type III stabilizers are employed in the present invention in the concentration level of between approximately 0.0001% to 2% by weight of the solution to be stabilized. The preferred concentration level of these Type III stabilizers is such that the pyridine or pyridone salt component (Type I) is present in said composition in an amount of from about 10 to about 1,000 parts per million, and the diphosphonate or methylenephosphonate salt component (Type II) is present in said composition in an amount of about 10 to about 3,000 parts per million (milligrams per kilogram) of the HAN-, HAN derivative- or hydroxylamine-containing composition to be stabilized.

In addition to the stabilizers within the scope of the present invention, ingredients such as those expected to form buffering solutions in acid media may be mixed with, for example, diphosphonate or methylenephosphonate salts, or the acids thereof. Examples of suitable buffer-forming compounds include dibasic ammonium citrate and bis(2-hydroxyethyl)iminotris(hydroxymethyl)-methane.

In accordance with the present invention, the stabilizers described above (Type I, Type II and Type III) may be suitably employed to stabilize HAN, HAN derivatives and hydroxylamine, as well as compositions comprising HAN, an HAN derivative or hydroxylamine. More specifically, the stabilizers within the scope of the present invention may be suitably employed in propellant compositions comprising HAN, an HAN derivative or hydroxylamine and various fuels, such as, for example only, triethanolammonium nitrate, diethylhydroxylammonium nitrate, or the trinitrate salt of tris(2-aminoethyl)amine.

The specific examples set forth herein are intended to merely illustrate the present invention. It will be obvious to those skilled in the art that changes and modifications may be made to these specific examples without departing from the spirit of this invention. The examples set forth below in no way are to be construed as limiting the scope of the invention herein.

EXAMPLE 1

(Type I Stabilizers)

I. Screening Tests

A. Sample Preparation: LP XM46+NaHPNO+Fe

A stock solution of iron-containing LP XM46 was prepared by weighing out 18.4 mg of ferric nitrate nonahydrate [Fe(NO$_3$)$_3$·9H$_2$O] and placing it into a 50 mL volumetric flask which was then filled to the 50 mL line with LP XM46 (specific gravity=1.45). An evaluation sample was prepared by weighing out 14.5 mg of NaHPNO. The 14.5 mg NaHPNO was placed in a one ounce Teflon PFA (perfluoroalkoxy) bottle to which 10 mL of the stock solution of iron-containing propellant, LP XM46+Fe, was pipetted in. The evaluation sample corresponds to a propellant composition comprising 0.1% wt. NaHPNO and 35 ppm of iron as a contaminant. This sample was shaken well and submitted for evaluation by Accelerated Rate Calorimetry (ARC). A separate sample of Neat LP XM46 and a sample of iron-containing LP XM46 stock solution were evaluated by ARC as well.

1) Accelerated Rate Calorimetry

In an ARC evaluation, a sample is placed in a sealed tantalum container in the adiabatic chamber of the instrument. The sample is heated to a predetermined temperature and held, while watching for any temperature exothermic reaction. If none is observed, the sample is further heated to the next predetermined temperature level. This process is repeated until an exothermic reaction is detected. The ARC method is very precise, having a detection level of 0.02 degrees per minute. The ARC evaluation was conducted for neat LP XM46 (no Fe), LP XM46 containing 35 ppm iron (as prepared above) and for the NaHPNO stabilizer evaluation sample (as prepared above), which contains 0.1% wt. NaHPNO, LP XM46 and 35 ppm iron.

The ARC onset temperature for neat LP XM46 was 125° C., while the onset temperature for LP XM46 with 35 ppm Fe was 112° C. ARC evaluation of the NaHPNO stabilizer evaluation sample had an onset temperature of 150° C.

It is clear from this ARC evaluation that NaHPNO has a stabilizing effect on LP XM46 with 35 ppm Fe. The fact that the NaHPNO sample composition which comprises NaHPNO, LP XM46 and 35 ppm Fe had an onset temperature higher than that for neat LP XM46 suggests that more than simple chelation of the iron is occurring, since the onset temperature is significantly higher than that for the neat LP XM46. This suggests that the iron complex of NaHPNO may be acting as a stabilizer in some additional, unanticipated fashion.

2) Acid Generation Rate Screening Test

Iron catalyzed decomposition of HAN-based propellants is accompanied by an increase in the nitric acid level, which further destabilizes the propellant composition. Hence, it is within the interest of the present invention to control the nitric acid level or inhibit the formation of nitric acid in these propellants; therefore, increasing their stability. The increase in acid as a function of time and iron content can be determined titrimetrically using standard techniques. This can be used to indirectly follow the effect of iron on the propellant system and of iron chelators, stabilizers, that inhibit the decomposition of the propellant.

The samples used were prepared as set forth in A, above, except that the iron concentration was adjusted to 50 ppm, as opposed to 35 ppm, in order to accelerate the rate of the experiment. Moreover, the stabilizers used to chelate the iron, so as to inhibit acid formation, were NaHPNO and the sodium salt of 2-mercaptopyridine-N-oxide (NaMPNO). Obviously when the sample using NaMPNO was prepared, NaMPNO was substituted for NaHPNO in A above. The samples were each placed in an oven at 65° C. for a total of 260 hours. Evaluation of the samples was conducted at various time intervals. The results of the acid build-up are presented in Table 2 and plotted in FIG. 1.

TABLE 2

Effect of Pyridine-N-oxide on Acid Generation
Rates in LP XM46

| Hours | LP + NaHPNO | LP + Fe | LP + NaHPNO + Fe | LP + NaMPNO | LP + NaMPNO + Fe |
|---|---|---|---|---|---|
| 0.25 | 0.035 | 0.08 | 0.04 | 0.035 | 0.035 |
| 66 | 0.02 | 0.14 | 0.04 | 0.01 | 0.1 |
| 116 | 0.03 | 0.2 | 0.045 | 0.1 | 0.15 |
| 260 | 0.055 | 0.46 | 0.05 | 0.105 | 0.32 | wherein LP=Liquid propellant LP XM46; NaHPNO= sodium salt of 2-hydroxy-pyridine-N-oxide; and NaMPNO= sodium salt of 2-mercapto-pridine-N-oxide.

Figure 1:
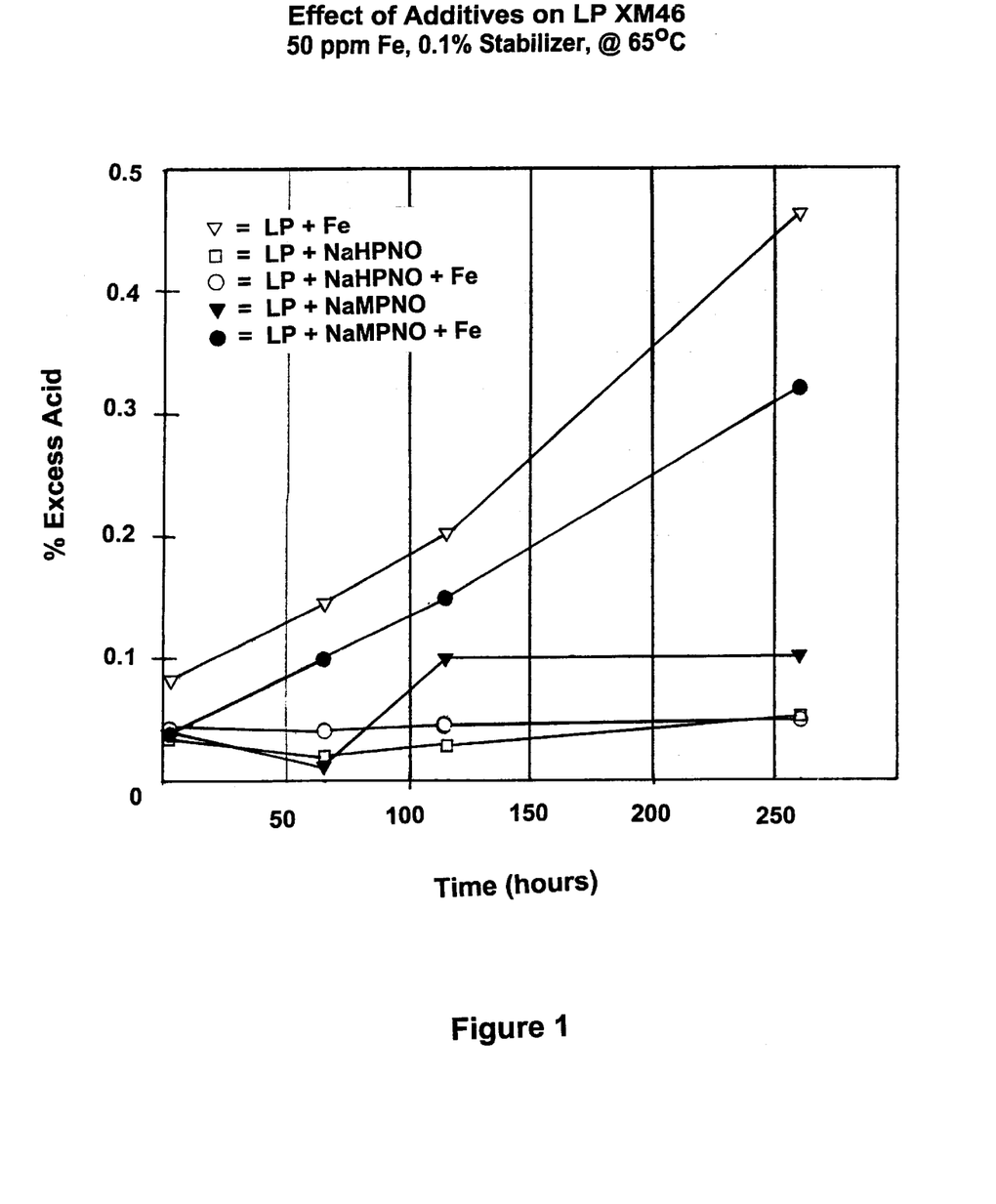
FIG. 1 illustrates the effect, over time, of substituted pyridine-N-oxides on the acid generation rates of compositions comprising the propellant LP XM46—Time (hours).

As can be seen from Table 2, and the accompanying FIG. 1, the addition of these stabilizers successfully reduces the acid generation rate in LP XM46, and, consequently, successfully acts to stabilize said propellant.

Stabilization of HAN Solutions

In addition to the testing of the stabilizers in the formulated propellant compositions set forth above, these stabilizers were evaluated in 82% HAN solutions. This is the concentration of the oxidizer commonly produced for use in the LP XM46.

27 mg of a 40% aqueous solution sodium mercaptopyridine-N-oxide (NaMPNO) was added to 10 grams of 82% HAN solution. The onset of decomposition of the resulting composition, as determined by ARC, was between 140° C. and 150° C. HAN, without the addition of NaMPNO, was determined to decompose at 126° C. The increased decomposition temperature provided by the NaMPNO-containing HAN composition illustrates the stabilizing effect of NaMPNO on said HAN containing composition.

II. Long Term Evaluation of Type I Stabilizer

A. Sample Preparation: LP XM46+NaHPNO+Fe

A double strength stock solution of LP XM46 containing 20 ppm Fe was prepared by weighing 211 mg of ferric nitrate nonahydrate [$Fe(NO_3)_3 \cdot 9H_2O$] and placing it in a polyethylene container to which 1460 g of LP XM46 was added. A second double strength stock solution containing 0.156% wt. NaHPNO was prepared by adding 250 mg of NaHPNO to 160 g of LP XM46.

A sample to be evaluated was prepared by mixing 80 g of the first stock solution (the Fe-containing stock solution) with 80 g of the second stock solution (the NaHPNO-containing solution) in a polyethylene bottle. This sample results in a LP XM46 sample containing 0.078% wt. NaHPNO and 10 ppm Fe.

An additional sample to be evaluated was prepared by mixing 73 g of the second stock solution (the NaHPNO-containing solution) with 73 g of LP XM46 in a polyethylene bottle. This resulting LP XM46 solution contains 0.078% wt. NaHPNO without Fe.

The evaluation samples tested can be summarized as follows:

a) Neat LP XM46 (control with no Fe present)
b) 1:1 mixture of Neat LP XM46 and the double strength stock solution of LP XM46 containing 20 ppm Fe=LP XM46+10 ppm Fe (Fe control)
c) 1:1 mixture of Neat LP XM46 and the double strength stock solution containing NaHPNO=LP XM46+ 0.078% wt. NaHPNO; and
d) 1:1 mixture of double strength stock solution of LP XM46 containing 20 ppm Fe and the double strength stock solution containing NaHPNO=LP XM46+ 0.078% wt. NaHPNO+10 ppm Fe 1) Sample Aging and Analysis for Acid Generation The samples set forth in A, above, were evaluated for their acid generation. Each sample was transferred to a 125 mL Teflon PFA bottle and sealed so as to avoid contamination of their contents during the testing procedure. The bottles containing the samples were then placed in a 50° C. water bath. Heating samples of LP XM46 at elevated temperatures is a standard technique for simulating the effect of long-term aging on the propellant as well as accelerating the rate of propellant decomposition.

Figure 2:
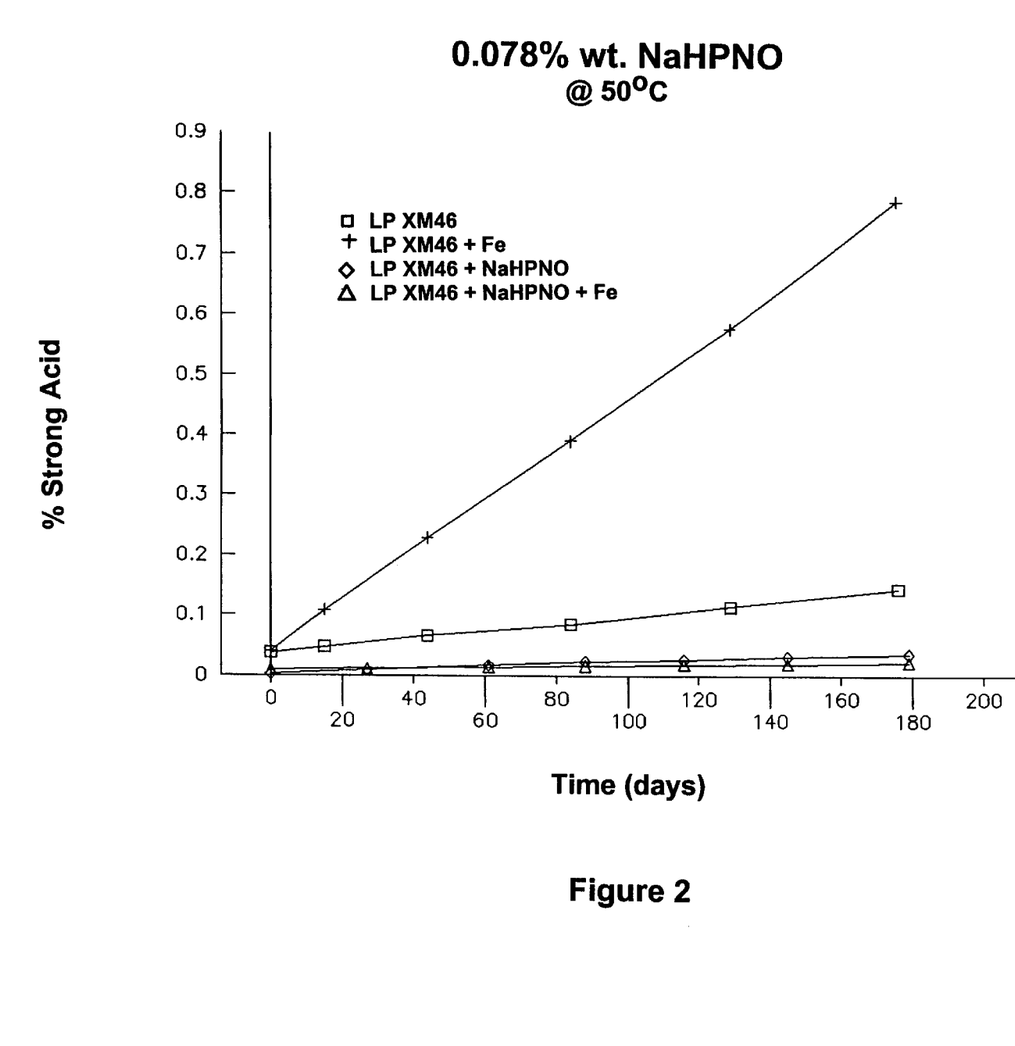
FIG. 2 illustrates the effect, over time, of the sodium salt of 2-hydroxypyridine-N-oxide (NaHPNO) on the acid generation rate of compositions comprising the propellant LP XM46—Time (days).

Decomposition of HAN-containing propellants, whether the propellants start out as containing iron or not, is accompanied by an increase in nitric acid concentration. In the propellant samples containing iron, the iron acts as a catalyst in the decomposition of the propellant and accordingly in the generation of nitric acid. As the nitric acid level increases, further destabilization of the HAN-containing propellant occurs. The increase in the concentration of nitric acid, as a function of time, can be used to follow the effect of iron on the propellant stability and on the effectiveness of the stabilizer (i.e., NaHPNO) used in inhibiting or reducing the generation of the acid, and therefore, inhibiting the decomposition of the sample propellant. The sample compositions comprising the stabilizer were evaluated for excess acid by taking monthly aliquots of approximately 10 ml from each sample and analyzing them for excess acid using standard titrimetric techniques. The results of the analysis and the relative rates of acid generation for the test samples comprising the stabilizer and those not are plotted in FIG. 2. Note from FIG. 2 that the presence of NaHPNO in the propellant compositions, both with and without iron, dramatically reduced the generation of acid.

The effect of NaHPNO on the relative rate of acid generation in said compositions as well as the relative life of said propellant compositions based on these rates are set forth in Table 3 and Table 4. The rates are normalized to the control identified at the subheading of each Table—i.e., Table 3a is normalized to LP XM46 wherein the relative rate of acid generation for LP XM46 is 100% and its relative life is 100%. The lower relative rates of acid generation in compositions containing the stabilizers tested indicate their ability to effectively stabilize LP XM46.

Further examples of stabilizers within the scope of the present invention are set forth below.

EXAMPLE 2

(Type II Stabilizers)

I. Long Term Evaluation of Type II Stabilizers

A. Sample Preparation: LP XM46+Type II Stabilizer+Fe

A double strength stock solution of LP XM46 containing 20 ppm Fe was prepared by weighing 211 mg of ferric nitrate nonahydrate [$Fe(NO_3)_3 \cdot 9H_2O$] and placing it in a polyethylene container to which 1460 g of LP XM46 was added. A second double strength stock solution containing 0.2% wt. Dequest 2054 was prepared by adding 320 mg of Dequest 2054 to 160 g of LP XM46.

An evaluation sample was prepared by mixing 80 g of the first stock solution (the Fe-containing stock solution) with 80 g of the second stock solution (the Dequest 2054-containing solution) in a polyethylene bottle. This first sample results in a LP XM46 sample containing 0.1% wt. Dequest 2054 and 10 ppm Fe.

A second evaluation sample was prepared by mixing 73 g of the second stock solution (the Dequest 2054-containing solution) with 73 g of LP XM46 in a polyethylene bottle. This resulting LP XM46 solution contains 0.1 % wt. Dequest 2054 without Fe.

Additional evaluation samples were prepared wherein Dequest 2010, Dequest 2016D, and Dequest 2051 were individually used in place of Dequest 2054 above. These evaluation samples were prepared using the sample preparation method described above. A total of eight evaluation samples were prepared—4 LP XM46 samples containing one of each named Dequest with Fe; and 4 LP XM46 samples containing one of each named Dequest without Fe.

The samples evaluated can be summarized as prepared as follows:

a) Neat LP XM46 (control with no Fe present)
b) 1:1 mixture of Neat LP XM46 and the double strength stock solution of LP XM46 containing 20 ppm Fe=LP XM46+10 ppm Fe (Fe control)
c) 1:1 mixture of Neat LP XM46 and the double strength stock solution containing the candidate Type II stabilizer=LP XM46+0.1% wt. Type II stabilizer; and
d) 1:1 mixture of double strength stock solution of LP XM46 containing 20 ppm Fe and the double strength stock solution containing the candidate Type II stabilizer=LP XM46+0.1% wt. Type II stabilizer+10 ppm Fe.

1) Sample Aging and Analysis for Acid Generation

The samples set forth in A, above, were evaluated for their acid generation in the same manner used in the evaluation of Type I stabilizers, in Example 1, Part II, at paragraph 1.

Figure 3:
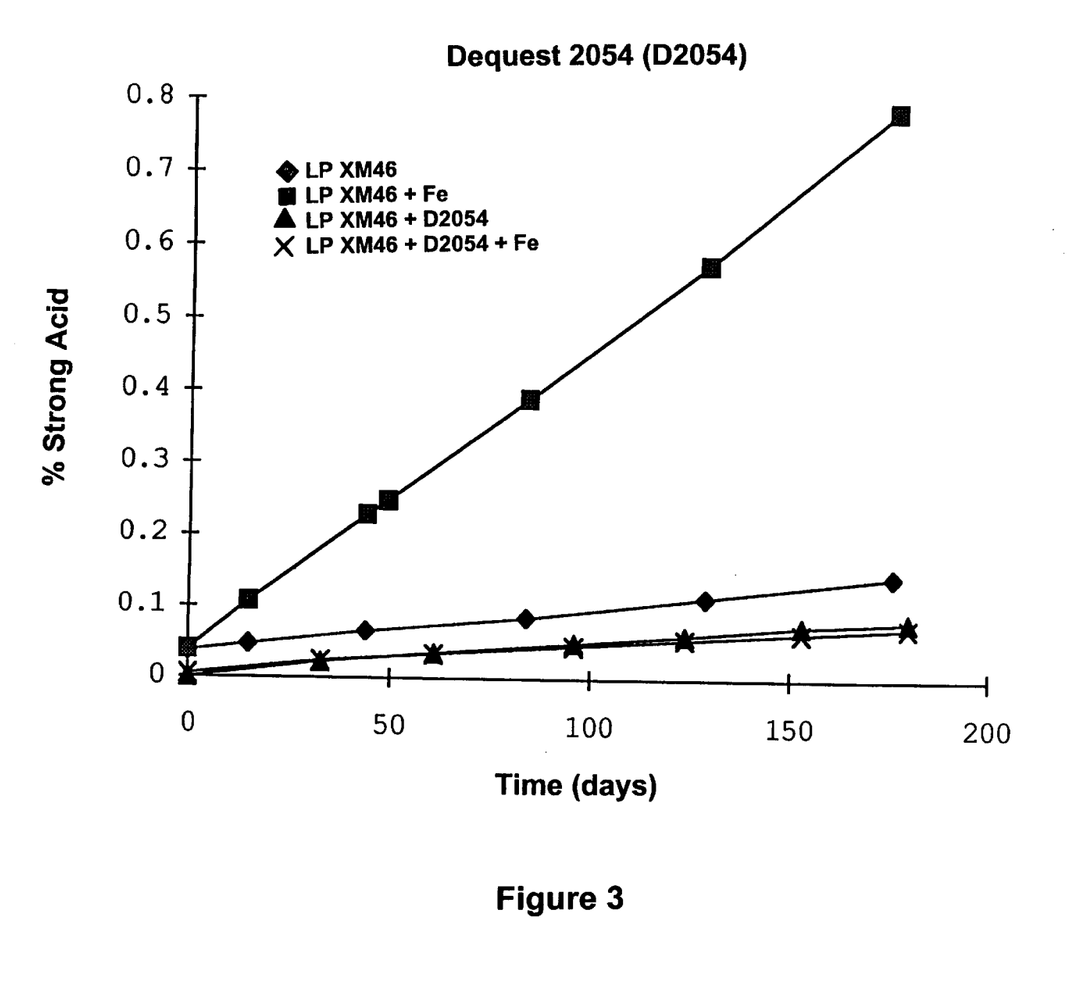
FIG. 3 illustrates the effect, over time, of the hexapotassium salt of hexamethylenediaminetetra (methylenephosphonic acid)—Dequest 2054—on the acid generation rate of compositions comprising the propellant LP XM46.

The effect of Dequest 2054 (D 2054) on the acid generation rate in LP XM46 over time is set forth in plot form in FIG. 3. Note that the presence of Dequest 2054 in the propellant composition reduces the rate of acid generation in the propellant.

The effect of all the Type II stabilizers tested on the relative rate of acid generation in said compositions as well as the relative life of said propellant compositions based on these rates are set forth in Table 3 and Table 4. The rates are normalized to the control identified at the subheading of each table. The lower relative rates of acid generation in compositions containing the stabilizers tested indicate their ability to effectively stabilize LP XM46.

TABLE 3

Effect of Stabilizers on Acid Generation Rates in LP XM46

| Sample = LP XM46 + | Time (mos.) | Relative Rate of Acid Generation | Relative Life |
|---|---|---|---|
| a) Normalized to LP XM46 as control (no Fe present) | | | |
| NaHPNO | 9 | 33% | 299% |
| D 2010 | 7 | 20% | 491% |
| D 2016D | 8 | 49% | 203% |
| D 2051 | 8 | 41% | 246% |
| D 2054 | 6 | 77% | 130% |
| b) Normalized to LP XM46 as control (no Fe present) | | | |
| NaHPNO + Fe | 9 | 13% | 752% |
| D 2010 + Fe | 7 | 101% | 99% |
| D 2016D + Fe | 8 | 157% | 64% |
| D 2051 + Fe | 8 | 47% | 211% |
| D 2054 + Fe | 6 | 62% | 161% |
| c) Normalized to LP XM46 + Fe control | | | |
| NaHPNO + Fe | 9 | 1.9% | 5,260% |
| D 2010 + Fe | 7 | 14% | 703% |
| D 2016D + Fe | 8 | 18% | 556% |
| D 2051 + Fe | 8 | 6.8% | 1,475% |
| D 2054 + Fe | 6 | 8.9% | 1,125% |

TABLE 4

Effect of Stabilizers on Acid Generation Rates in LP XM46 After 6 mos. @ 50° C.

| Sample = LP XM46 + | Relative Rate of Acid Generation | Relative Life |
|---|---|---|
| a) Normalized to LP XM46 as control (no Fe present) | | |
| NaHPNO | 31% | 320% |
| D 2010 | 23% | 440% |
| D 2016D | 43% | 230% |
| D 2051 | 39% | 260% |
| D 2054 | 66% | 150% |
| b) Normalized to LP XM46 control (no Fe present) | | |
| NaHPNO + Fe | 13% | 790% |
| D 2010 + Fe | 101% | 99% |
| D 2016D + Fe | 155% | 64% |
| D 2051 + Fe | 50% | 200% |
| D 2054 + Fe | 54% | 190% |
| c) Normalized to LP XM46 + Fe control | | |
| NaHPNO + Fe | 1.8% | 5,560% |
| D 2010 + Fe | 14% | 700% |
| D 2016D + Fe | 22% | 450% |
| D 2051 + Fe | 7.1% | 1,430% |
| D 2054 + Fe | 7.6% | 1,310% |

EXAMPLE 3

(Type III Stabilizers)

It has been discovered, and within the scope of the present invention, that a mixture of said Type I (pyridine or pyridone type) and Type II (Dequest type) stabilizers, described above, provides for an enhanced stabilizing effect on HAN, HAN derivatives and hydroxylamine and compositions comprising at least one of said HAN, HAN derivatives or hydroxylamine. The combination of said stabilizers, in specific proportions provides for a synergistic stabilizing effect on the types of compositions described herein. Moreover, it has been found and demonstrated by the present invention that a mixture of Type I and Type II stabilizers, specifically a mixture of Dequests and NaHPNO, can be used to adjust the initial acid level of LP XM46 during its manufacturing process so as to provide effective storage stable properties to the propellant. Samples of various stabilizer combinations were evaluated and prepared as set forth below.

Type III stabilizers comprise effective stabilizing amounts of Type I and Type II stabilizers. A method for determining the amounts of each Type I and Type II stabilizer to employ into said HAN-, HAN derivative-, or hydroxylamine-containing composition to provide an enhanced stabilizing effect is described herein.

I. LP XM46+NaHPNO+Dequest 2010+Dequest 2016D

A. Method to Adjust Initial Acidity of LP XM46 and Determine the Amounts of NaHPNO, Dequest 2010 and Dequest 2016D to Employ to Stabilize LP XM46

It has been specifically demonstrated that a mixture of NaHPNO, Dequest 2010, and Dequest 2016D can be used to adjust the initial acid level of LP XM46 during its manufacturing process. Adjusting the initial acid level of LP XM46 using this mixture has been found to provide for a propellant composition having greater stability properties. This combination of Type I and Type II stabilizers has been demonstrated as providing greater stability to propellant compositions than use of the individual stabilizer components themselves.

The synergistic effect has been demonstrated for compositions having specific proportions of said stabilizers. These proportions can be determined, for instance, in the following manner:

For example purposes only, when a solution of LP XM46 is made containing 0.1% wt. NaHPNO, the apparent acidity of the propellant decreases according to the following equation [1]:

$$\%\text{Apparent Acidity} = \%\text{Initial Acidity} - 0.045\% \quad [1]$$

Since the specification limits for acidity in acceptable propellants are 0<apparent acidity<0.05%, a "desired shift" is defined. The "desired shift" in acidity is the change in acidity required, as a result of applying equation [1], to adjust the total acidity back into this acceptable range. The "desired shift" may be obtained by simultaneously solving the following equations, [2] and [3], to determine the weight ratio of Dequest 2010 to Dequest 2016D to be added to the LP XM46 propellant composition already containing 0.1% wt. NaHPNO:

$$x + y = 82 \quad [2]$$

$$\frac{0.046x - 0.036y}{82} = \text{desired shift} \quad [3]$$

wherein x equals the number of parts by weight of Dequest 2010 and y equals the number of parts by weight of Dequest 2016D in an 82 part mixture of Dequest 2010 and Dequest 2016D. It is important to note that either x or y may equal zero, in which case the Type III stabilizer composition would comprise NaHPNO and a single Dequest component.

Use of these equations can be demonstrated as follows: If the desired shift in acidity is +0.01%, then solving equations [2] and [3] yields 46 parts by weight of Dequest 2010 of the 82 part mixture of Dequest 2010/Dequest 2016D and 36 parts by weight of Dequest 2016D. Stated differently, of the 82 parts of the Dequest 2010/Dequest 2016D mixture, 56.1% would be Dequest 2010 and 43.9% would be Dequest 2016D.

If the desired target of Dequest 2016D alone had been 0.1% (amount of active anion to sequester approximately 100 ppm Fe), only 0.048% of Dequest 2016D is added. Similarly, if the desired target of Dequest 2010 alone had been 0.118% (equivalent to the same number of moles of anion as 0.1% Dequest 2016D), only 0.062% of Dequest 2010 is added. To meet the desired shift in acidity of 0.01%, 165 mg of NaHPNO, 102 mg of Dequest 2010, and 80 mg of Dequest 2016D is added to 165 grams of LP XM46.

Given the interrelationship set forth above between the specific stabilizer ingredients in this Type III stabilizer and depending on the initial acid content of a propellant, one skilled in the art would be able to adjust the concentration of stabilizer components needed to achieve a stable propellant composition.

B. Sample Preparation: LP XM46+NaHPNO+Dequest 2010+Dequest 2016D Both With and Without Fe A double strength stock solution of LP XM46 containing 20 ppm Fe was prepared by weighing out 211 mg of ferric nitrate nonahydrate [$Fe(NO_3)_3 \cdot 9H_2O$] and placing it a polyethylene container. To said container, 1460 grams of LP XM46 was added.

A second double strength stock solution was prepared containing 0.2% wt. NaHPNO, 0.124% wt. Dequest 2010, and 0.096% wt. Dequest 2016D. This was prepared by adding 330 mg of NaHPNO, 204 mg of Dequest 2010 and 160 mg of Dequest 2016D to 330 grams of LP XM46.

An evaluation sample was prepared by mixing 80 grams of the first stock solution containing Fe with 80 grams of the second stock solution containing the stabilizers in a polyethylene bottle. This resulted in an LP XM46 evaluation sample containing 0.1% wt. NaHPNO, 0.062% wt. Dequest 2010 and 0.048% wt. Dequest 2016D and 10 ppm Fe.

An additional evaluation sample was prepared by mixing 80 grams of the second stock solution containing the stabilizers with 80 grams of LP XM46 (no Fe) in a polyethylene bottle. This resulting second LP XM46 evaluation solution contained 0.1% wt. NaHPNO, 0.062% wt. Dequest 2010 and 0.048% wt. Dequest 2016D. Note that no Fe is present initially in this evaluation sample.

The samples evaluated herein can be summarized as follows:
  a) Neat LP MX46 (control with no Fe present)
  b) 1:1 mixture of Neat LP XM46 and double strength stock solution of LP XM46 containing 20 ppm Fe=LP XM46+10 ppm Fe (Fe control)
  c) 1:1 mixture of Neat LP XM46 and the double strength stock solution containing NaHPNO, Dequest 2010 and Dequest 2016D=LP XM46+NaHPNO/D2010/D2016D
  d) 1:1 mixture of double strength stock solution of LP XM46 containing 20 ppm Fe and double strength stock solution containing NaHPNO, Dequest 2010 and Dequest 2016D=LP XM46+NaHPNO/D2010/D2016D/Fe 1) Sample Aging and Evaluation for Acid Generation Each sample from B, above, was evaluated for their acid generation in the same manner described in the evaluation of Type I stabilizers in Example 1, Part II, at paragraph 1.

Figure 4:
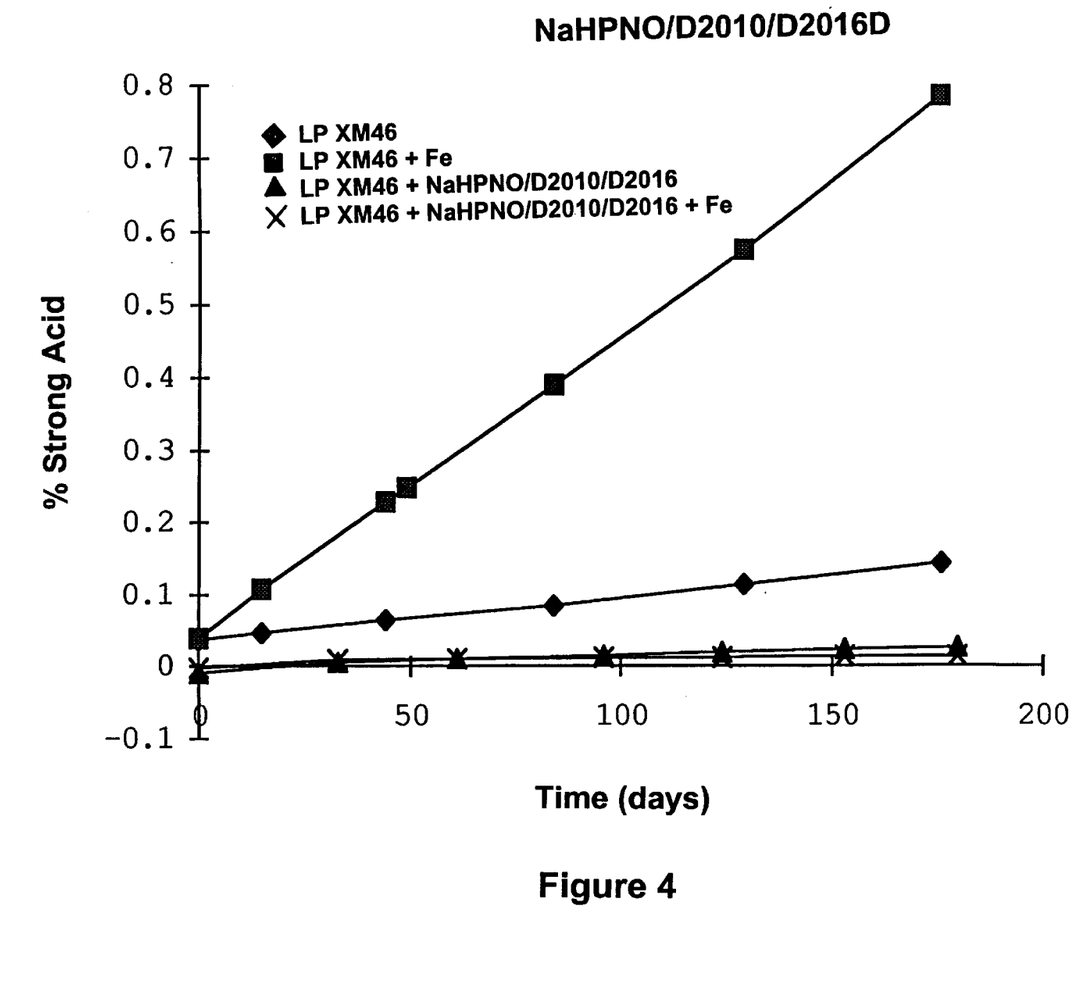
FIG. 4 illustrates the effect, over time, of the stabilizer mixture NaHPNO/D2010/D2016D on the acid generation rate of the propellant LP XM46.

The effect of the stabilizer mixtures containing NaHPNO, Dequest 2010 and Dequest 2016D on the relative rates of acid generation in the compositions described is presented in Table 5 and Table 6 below. The relative rates of acid generation are plotted in FIG. 4. Table 5 and Table 6 data further provide estimates of relative storage life based on the evaluated rates. Once again, the rates are normalized to the control stock solutions, LP XM46 (no Fe) and LP XM46+Fe, provided in B above. The lower relative rates of acid generation in compositions containing the stabilizer mixtures demonstrates the ability of these mixtures to stabilize LP XM46.

Note that the stabilizer combination containing NaHPNO, Dequest 2010, and Dequest 2016D demonstrates not only the mixture's ability to stabilize LP XM46, but the experimental data illustrates a synergistic stabilizing effect for said combination of ingredients. (Synergy is observed by evaluating the data set forth in Table 5 and Table 6 as compared to Table 4.)

II. LP XM46+NaHPNO+Dequest 2051+Dequest 2054

A. Method to Adjust Initial Acidity of LP XM46 and Determine the Amounts of NaHPNO, Dequest 2051 and Dequest 2054 to Employ to Stabilize LP XM46

It has been specifically demonstrated that a mixture of NaHPNO, Dequest 2051, and Dequest 2054 can be used to adjust the initial acid level of LP XM46 during its manufacturing process. As with the previous Type III stabilizer composition, adjusting the initial acid level of LP XM46 using this mixture provides for a propellant composition having greater stability properties. This combination of stabilizers has been demonstrated as providing greater stability to propellant compositions than the individual stabilizer components themselves.

Synergistic stabilizing effect has been demonstrated for compositions having specific proportions of these stabilizers, which can be determined, for instance, in the following manner:

As previously described, when a solution of LP XM46 is made containing 0.1% wt. NaHPNO, the apparent acidity of the propellant decreases according to the following equation [1]:

%Apparent Acidity=%Initial Acidity−0.045%  [1]

Since the specification limits for acidity in acceptable propellants are 0<apparent acidity<0.05%, a "desired shift" is defined. The "desired shift" in acidity is the change in acidity required, as a result of applying equation [1], to adjust the total acidity back into this acceptable range of 0<apparent acidity<0.05%. The "desired shift" may be obtained by simultaneously solving the following equations, [2] and [3], to determine the weight ratio of Dequest 2051 to Dequest 2054 to be added to the LP XM46 propellant composition already containing 0.1% wt. NaHPNO:

$$x+y=77 \quad [2]$$

$$\frac{0.044x - 0.033y}{77} = \text{desired shift} \quad [3]$$

wherein x equals the number of parts by weight of Dequest 2051 and y equals the number of parts by weight of Dequest 2054 in a 77 part mixture of Dequest 2051 and Dequest 2054. It is important to note that either x or y may equal zero, in which case the Type III stabilizer composition would comprise NaHPNO and a single Dequest component.

Use of these equations can be demonstrated as follows: If the desired shift in acidity is +0.01%, then solving equations [2] and [3] yields 46 parts by weight of Dequest 2051 of the 77 part mixture of Dequest 2051/Dequest 2054 and 31 parts by weight of Dequest 2054. Stated differently, of the 77 parts of the Dequest 2051/Dequest 2054 mixture, 59.7% would be Dequest 2051 and 40.3% would be Dequest 2054.

To meet the desired shift in acidity of 0.01 %, the propellant composition would comprise 0.1% wt. NaHPNO, 0.153% wt. D2051 and 0.103% wt. D2054. Note that the equations employed for this Type III stabilizer are different than those used in the previous Type III stabilizer example.

Once again, given the interrelationship set forth above between the specific stabilizer ingredients in this Type III stabilizer and depending on the initial acid content of a propellant, one skilled in the art would be able to adjust the concentration of these stabilizer components needed to achieve a stable propellant composition.

B. Sample Preparation: LP XM46+NaHPNO+Dequest 2051+Dequest 2054 Both With and Without Fe Samples similar to those prepared above for the Type III stabilizer composition comprising LP XM46+NaHPNO+Dequest 2010+Dequest 2016D were prepared but substituting Dequest 2051 and Dequest 2054 for the Dequest 2010 and Dequest 2016D used. These samples were made in the same fashion as described above except that the concentrations of Dequest 2051 and Dequest 2054 used were equimolar to those employed for Dequest 2010 and Dequest 2016D in the previous sample preparation.

Employing the preparation method described resulted in LP XM46 evaluation samples containing (1) 0.1% wt. NaHPNO, 0.153% wt. Dequest 2051, 0.103% wt. Dequest 2054 and 10 ppm Fe; and (2) 0.1% wt. NaHPNO, 0.153% wt. Dequest 2051 and 0.103% wt. Dequest 2054 (with no Fe). Neat LP XM46 and a propellant composition comprising LP XM46 plus 10 ppm Fe were also used for evaluation.

1) Sample Evaluation for Acid Generation

Each of the samples from B above, were then evaluated for acid generation using the same methodology described as being used for the evaluation of the samples comprising LP XM46+NaHPNO+Dequest 2010+Dequest 2016D.

The relative rates of acid generation for these samples are presented in Table 5 and Table 6 below. These Tables further provide estimates for relative storage life for these stabilized compositions based on the evaluated acid generation rates. It is important to note that the rates are normalized to the control stock solutions of LP XM46 (No Fe) and LP XM46+Fe. The lower relative rates of acid generation in compositions containing the stabilizer mixtures demonstrates the ability of these mixtures to stabilize LP XM46.

As with the stabilizer combination containing NaHPNO, Dequest 2010 and Dequest 2016D, the stabilizer combination herein has been shown as having not only a stabilizing effect on LP XM46, but also as providing a synergistic stabilizing effect.

TABLE 5

Effect of Type III Stabilizers on Acid Generation Rates in LP XM46

| Sample = LP XM46 + | Time (mos.) | Relative Rate of Acid Generation | Relative Life |
|---|---|---|---|
| a) Normalized to LP XM46 (no Fe present) | | | |
| NaHPNO/D2010/D2016D | 6 | 27% | 366% |
| NaHPNO/D2051/D2054 | 6 | 22% | 445% |
| BisTris/D2010/D2016D | 7 | 52% | 194% |
| AmmCitrate/D2010/D2016 | 7 | 49% | 204% |
| b) Normalized to LP XM46 (no Fe Present) | | | |
| NaHPNO/D2010/D2016D/Fe | 6 | 6.3% | 1,593% |
| NaHPNO/D2051/D2054/Fe | 6 | 5.3% | 1,884% |
| BisTris/D2010/D2016D/Fe | 7 | 142% | 71% |
| AmmCitrate/D2010/D2016D/Fe | 7 | 142% | 70% |
| c) Normalized to LP XM46 + Fe (Fe present in control) | | | |
| NaHPNO/D2010/D2016D/Fe | 6 | 0.90% | 11,139% |
| NaHPNO/D2051/D2054/Fe | 6 | 0.75% | 13,177% |
| BisTris/D2010/D2016D/Fe | 7 | 20% | 492% |
| AmmCitrate/D2010/D2016D/Fe | 7 | 20% | 491% |

TABLE 6

Effect of Stabilizer Mixes (Type III) on Acid Generation Rates in LP XM46 after 6 mos. @ 50° C.

| Sample = LP XM46 + | Relative Rate of Acid Generation | Relative Life |
|---|---|---|
| a) Normalized to LP XM46 control (no Fe present) | | |
| NaHPNO/D2010/D2016D | 24% | 420% |
| NaHPNO/D2051/D2054 | 21% | 470% |
| BisTris/D2010/D2016D | 58% | 170% |
| AmmCitrate/D2010/D2016D | 45% | 220% |
| b) Normalized to LP XM46 control (no Fe present) | | |
| NaHPNO/D2010/D2016D/Fe | 4.6% | 2,160% |
| NaHPNO/D2051/D2054/Fe | 5.9% | 1,700% |
| BisTris/D2010/D2016D/Fe | 132% | 76% |
| AmmCitrate/D2010/D2016D/Fe | 131% | 77% |
| c) Normalized to LP XM46 + Fe control (Fe present) | | |
| NaHPNO/D2010/D2016D/Fe | 0.90% | 15,100% |
| NaHPNO/D2051/D2054/Fe | 0.76% | 11,900% |
| BisTris/D2010/D2016D/Fe | 19% | 530% |
| AmmCitrate/D2010/D2016D/Fe | 19% | 540% |

EXAMPLE 4

I. Stabilization of HAN and HAN Derivative Based Propellants

It has been demonstrated above that a stabilizer mixture of NaHPNO with Dequests can be successfully used to adjust the initial acid level of LP XM46 during its manufacturing process. It has further been demonstrated that these stabilizer mixtures were even more effective as stabilizers in LP XM46 than their individual component ingredients— synergy was observed. This example will illustrate that mixtures of these stabilizers are effective as stabilizers when used in other high energy propellant systems containing HAN and an HAN derivative. Propellant systems having higher energy than LP XM46 were selected for further evaluation of these stabilizers. The selected propellants are LGP 4640 and LGP 4440. The composition of these propellants is set forth in Table 1.

A. Sample Preparation: Propellant+Type III Stabilizer

The propellants employed herein are LGP 4640 and LGP 4440. Double strength stock solutions of LGP 4640 and LGP 4440 containing 20 ppm Fe and 40 ppm Fe were prepared using Fisher A.C.S. Certified Fe $(NO_3)_3 \cdot 9H_2O$ in a fashion similar to that described in Example 2 for LP XM46.

To these propellant compositions, double strength stock solutions of candidate stabilizers to be evaluated were added. Candidate stabilizers used are mixtures comprising NaHPNO, Dequest 2010 and Dequest 2016D; and mixtures comprising only Dequest 2010 and Dequest 2016D (without NaHPNO).

The stabilizer composition represented as HDD(A) in the table below, comprises NaHPNO, Dequest 2010 and Dequest 2016D, wherein the weight ratio of Dequest 2010 to Dequest 2016D is 1.29:1. The weight ratio of NaHPNO to the combination of Dequests is approximately 1:1. An additional stabilizer composition, designated as HDD(B), was evaluated wherein the weight ratio of Dequest 2010 to Dequest 2016D is 0.35:1. Once again, the weight ratio of NaHPNO to this Dequest combination is approximately 1:1. The stabilizers DD(A) and DD(B) referenced below represent stabilizer compositions comprising merely Dequest 2010 and Dequest 2016D (the NaHPNO is eliminated). The weight ratio of Dequest 2010 to Dequest 2016D in DD(A) is 1.29:1; whereas the weight ratio of Dequest 2010 to Dequest 2016D in DD(B) is 0.35:1.

The following sample compositions were evaluated:

a) Neat LGP 4640 (no Fe) or Neat LGP 4440 (no Fe);

b) A 1:1 mixture of Neat LGP 4640 or LGP 4440 and the double strength stock Fe solution of each individually to make (LGP 4640+10 ppm (or 20 ppm) Fe) or (LGP 4440+10 ppm (or 20 ppm) Fe)—(Fe control for each propellant)

c) A 1:1 mixture of Neat LGP 4640 or Neat LGP 4440 and the double strength stabilizer solution to make (LGP 4640+stabilizer) or (LGP 4440+stabilizer)—no Fe is present d) A 1:1 mixture of double-strength LGP 4640 or LGP 4440+Fe solution and the double-strength candidate stabilizer solution to make ((LGP 4640 or LGP 4440)+stabilizer+Fe)

The final compositions of the propellant evaluation samples employing HDD(A) as the stabilizer comprise 0.1% wt. NaHPNO, 0.062% wt. Dequest 2010 and 0.048% wt. Dequest 2016D. Final propellant evaluation samples containing HDD(B) comprise 0.1% wt. NaHPNO, 0.027% wt. Dequest 2010 and 0.078% wt. Dequest 2016D. Moreover, the final evaluation samples containing DD(A) and DD(B) as stabilizers are as follows:

a) LGP 4640+DD(A)—0.155% wt. D 2010; 0.121% wt. D 2016D b) LGP 4640+DD(B)—0.054% wt. D 2010; 0.156% wt. D 2016D c) LGP 4440+DD(B)—0.195% wt. D 2010; 0.067% wt. D 2016D

All samples were stored at −15° C. in Teflon PFA bottles to minimize reaction prior to evaluation. These candidate propellant systems to be evaluated are set forth below in Table 7.

TABLE 7

Candidate Liquid Propellant Systems*

| Propellant | Stabilizer Mixture | Iron Contamination |
|---|---|---|
| LGP 4640 | HDD(A) | 10 ppm |
| LGP 4640 | HDD(B) | 10 and 20 ppm |
| LGP 4640 | DD(A) | 10 ppm |
| LGP 4640 | DD(B) | 10 ppm |
| LGP 4440 | DD(B) | 10 ppm |

*These liquid propellant systems were tested both with and without the presence of initial iron contamination.

The results of the evaluation of these propellant systems is set forth below.

TABLE 8

Effect of Stabilizers on Acid Generation Rates in LGP 4640 or LGP 4440 after 6 mos. @ 50° C.

| Propellant System | Relative Rate of Acid Generation | Relative Life |
|---|---|---|
| a) Normalized to either LGP 4640 or LGP 4440 as appropriate (no Fe present) | | |
| 4640 | 100% | 100% |
| 4640 + HDD(A) | 33% | 310% |
| 4640 + HDD(B) | 40% | 250% |
| 4640 + DD(A) | 23% | 440% |
| 4640 + DD(B) | 45% | 220% |
| 4440 + DD(B) | 23% | 440% |
| b) Normalized to either LGP 4640 or LGP 4440 as appropriate (no Fe present) | | |
| 4640 + 10 ppm Fe | 686% | 18% |
| 4640 + HDD(A) + 10 ppm Fe | 31% | 330% |
| 4640 + HDD(B) + 10 ppm Fe | 30% | 330% |
| 4640 + HDD(B) + 20 ppm Fe | 34% | 300% |
| 4640 + DD(A) + 10 ppm Fe | 133% | 75% |
| 4640 + DD(B) + 10 ppm Fe | 169% | 60% |
| 4440 + DD(B) + 10 ppm Fe | 108% | 90% |
| c) Normalized to (LGP 4640 + 10 ppm Fe) or (LGP 4640 + 20 ppm Fe) or (LGP 4440 + 10 ppm Fe) as appropriate | | |
| 4640 + 10 ppm Fe | 100% | 100% |
| 4640 + HDD(A) + 10 ppm Fe | 4.5% | 2,240% |
| 4640 + HDD(B) + 10 ppm Fe | 4.4% | 2,290% |
| 4640 + HDD(B) + 20 ppm Fe | 4.9% | 2,030% |
| 4640 + DD(A) + 10 ppm Fe | 19% | 520% |
| 4640 + DD(B) + 10 ppm Fe | 25% | 400% |
| 4440 + DD(B) + 10 ppm Fe | 16% | 640% |

The propellants above were evaluated for acid generation and stability using the stabilizer combinations determined to be preferred during the LP XM46 studies conducted. Based on the data presented, it has been shown that the stabilizers within the scope of the present invention are effective as stabilizers in various types of HAN-, HAN derivative- and hydroxylamine-containing propellants. Specifically, this example illustrates the effectiveness of the stabilizers for HAN derivative based propellants (i.e., DEHAN containing propellants).

While particular embodiments of the present invention have been shown and described, it will be obvious to those skilled in the art that changes and modifications may be made without departing from this invention. Therefore, it is intended that the claims herein are to include all such obvious changes and modifications as fall within the true spirit and scope of this invention.

We claim:

1. A stabilized hydroxylammonium nitrate-, hydroxylammonium nitrate derivative- or hydroxylamine-containing composition consisting of said hydroxylammonium nitrate, hydroxylammonium nitrate derivative or hydroxylamine and a stabilizing effective amount of a pyridine salt, or an acid derivative thereof.

2. The composition of claim 1, wherein said pyridine salt, or acid derivative thereof, is present in said composition in an amount of between approximately 0.0001% by weight to 2% by weight.

3. The composition of claim 1, wherein said pyridine salt, or acid derivative thereof, is present in said composition in an amount of between approximately 10 to approximately 1,000 parts per million.

4. The composition of claim 1, wherein said pyridine salt is the sodium salt of 2-hydroxypyridine-N-oxide.

5. A process for stabilizing hydroxylammonium nitrate, a hydroxylammonium nitrate derivative, or hydroxylamine or a composition consisting of hydroxylammonium nitrate, a hydroxylammonium nitrate derivative or hydroxylamine against unwanted decomposition, which comprises adding to said hydroxylammonium nitrate, hydroxylammonium nitrate derivative or hydroxylamine or compositions consisting of hydroxylammonium nitrate, an hydroxylammonium nitrate derivative or hydroxylamine an effective stabilizing amount of a pyridine salt, or an acid derivative thereof, to provide a storage stable composition.

6. The process of claim 5, wherein said pyridine salt, or acid derivative thereof is present in said storage stable composition in an amount of between approximately 0.0001% wt. to 2% wt.

7. The process of claim 5, wherein said pyridine salt, or acid derivative thereof, is present in said storage stable composition in an amount of between approximately 10 to approximately 1,000 parts per million.

8. The process of claim 5, wherein said pyridine salt is the sodium salt of 2-hydroxypyridine-N-oxide.

9. A stabilized hydroxylammonium nitrate-, hydroxylammonium nitrate derivative- or hydroxylamine-containing composition consisting of said hydroxylammonium nitrate, hydroxylammonium nitrate derivative or hydroxylamine and a stabilizing effective amount of a diphosphonate or methylenephosphonate salt, or an acid derivative thereof.

10. The composition of claim 9, wherein said diphosphonate or methylenephosphonate salt, or acid derivative thereof, is present in said composition in an amount of between approximately 0.0001% by weight to 2% by weight.

11. The composition of claim 9, wherein said diphosphonate or methylenephosphonate salt, or acid derivative thereof, is present in said composition in an amount of between approximately 10 to approximately 3,000 parts per million.

12. The composition of claim 9, wherein said diphosphonate or methylenephosphonate salt, or acid derivative thereof, is 1-hydroxyethylidene-1,1-diphosphonic acid, or its corresponding tetrasodium salt.

13. The composition of claim 9, wherein said diphosphonate or methylenephosphonate salt is hexamethylenediaminetetra(methylenephosphonic acid), or its corresponding hexapotassium salt.

14. The composition of claim 9, wherein said diphosphonate or methylenephosphonate salt is aminotri(methylenephosphonic acid), or its corresponding pentasodium salt.

15. The composition of claim 9, wherein said diphosphonate or methylenephosphonate salt is diethylenetriaminepenta(methylenephosphonic acid), or its corresponding hexasodium salt.

16. A process for stabilizing hydroxylammonium nitrate, a hydroxylammonium nitrate derivative, or hydroxylamine or a composition consisting of hydroxylammonium nitrate, a hydroxylammonium nitrate derivative or hydroxylamine against unwanted decomposition, which consisting of adding to said hydroxylammonium nitrate, hydroxylammonium nitrate derivative or hydroxylamine or compositions consisting of hydroxylammonium nitrate, a hydroxylammonium nitrate derivative or hydroxylamine an effective stabilizing amount of a diphosphonate or methylenephosphonate salt, or an acid derivative thereof, to provide a storage stable composition.

17. The process of claim 16, wherein said diphosphonate or methylenephosphonate salt, or acid derivative thereof, is present in said storage stable composition in an amount of between approximately 0.0001% wt. to 2% wt.

18. The process of claim 16, wherein said diphosphonate or methylenephosphonate salt, or acid derivative thereof, is present in said storage stable composition in an amount of between approximately 10 to approximately 3,000 parts per million.

19. The process of claim 16, wherein said diphosphonate or methylenephosphonate salt, or acid thereof, is 1-hydroxyethylidene-1,1-diphosphonic acid, or its corresponding tetrasodium salt.

20. The process of claim 16, wherein said diphosphonate or methylenephosphonate salt, or acid derivative thereof, is hexamethylenediaminetetra(methylenephosphonic acid), or its corresponding hexapotassium salt.

21. The process of claim 16, wherein said diphosphonate or methylenephosphonate salt, or acid derivative thereof, is aminotri(methylenephosphonic acid), or its corresponding pentasodium salt.

22. The process of claim 16, wherein said diphosphonate or methylenephosphonate salt, or acid thereof, is diethylenetriaminepenta(methylenephosphonic acid), or its corresponding hexasodium salt.

23. A stabilized hydroxylammonium nitrate-, hydroxylammonium nitrate derivative-, or hydroxylamine-containing composition consisting of said hydroxylammonium nitrate, hydroxylammonium nitrate derivative or hydroxylamine and a stabilizing effective amount of a stabilizer mixture consisting of (a) at least one pyridine salt, or an acid derivative thereof; and (b) at least one diphosphonate or methylenephosphonate salt, or acid derivative thereof.

24. The composition of claim 23, wherein said stabilizer mixture is present in said composition in an amount of between approximately 0.0001% wt. to 2% wt.

25. The composition of claim 23, wherein said at least one pyridine or salt, or acid derivative thereof, is present in said composition in an amount between approximately 10 to approximately 1,000 parts per million; and wherein said at least one diphosphonate or methylenephosphonate salt, or acid derivative thereof, is present in said composition in an amount of between approximately 10 to approximately 3,000 parts per million.

26. The composition of claim 23, wherein said pyridine salt is the sodium salt of 2-hydroxypyridine-N-oxide.

27. The composition of claim 23, wherein said at least one diphosphonate or methylenephosphonate salt, or acid thereof, is selected from 1-hydroxyethylidene-1,1-diphosphonic acid, or its corresponding tetrasodium salt.

28. The composition of claim 23, wherein said at least one diphosphonate or methylenephosphonate salt, or acid derivative thereof, is selected from hexamethylenediaminetetra(methylenephosphonic acid), or its corresponding hexapotassium salt.

29. The composition of claim 23, wherein said at least one diphosphonate or methylenephosphonate salt, or acid derivative thereof, is selected from aminotri (methylenephosphonic acid), or its corresponding pentasodium salt.

30. The composition of claim 23, wherein said at least one diphosphonate or methylenephosphonate salt, or acid derivative thereof, is selected from diethylenetriaminepenta (methylenephosphonic acid), or its corresponding hexasodium salt.

31. A process for stabilizing hydroxylammonium nitrate, a hydroxylammonium nitrate derivative, or hydroxylamine or a composition consisting of hydroxylammonium nitrate, a hydroxylammonium nitrate derivative or hydroxylamine against unwanted decomposition, which consists of adding to said hydroxylammonium nitrate, hydroxylammonium nitrate derivative or hydroxylamine or compositions comprising hydroxylammonium nitrate, a hydroxylammonium nitrate derivative or hydroxylamine a stabilizing effective amount of a stabilizer mixture consisting of (a) at least one pyridine salt, or an acid derivative thereof; and (b) at least one diphosphonate or methylenephosphonate salt, or acid derivative thereof to provide a storage stable composition.

32. The process of claim 31, wherein said stabilizer mixture is present in said storage stable composition in an amount of between approximately 0.0001% wt. to 2% wt.

33. The process of claim 31, wherein said at least one pyridine salt, or acid thereof, is present in said storage stable composition in an amount between approximately 10 to approximately 1,000 parts per million; and wherein said at least one diphosphonate or methylenephosphonate salt, or acid derivative thereof, is present in said storage stable composition in an amount of between approximately 10 to approximately 3,000 parts per million.

34. The process of claim 31, wherein said pyridine or pyridone salt is the sodium salt of 2-hydroxypyridine-N-oxide.

35. The process of claim 31, wherein said pyridine or pyridone salt is selected from the group consisting of zinc pyrithione, copper pyrithione, manganese pyrithione; nickel pyrithione; cobalt pyrithione, bismuth pyrithione; zirconium pyrithione and 1-hydroxy-6-substituted pyridiones.

36. The process of claim 31, wherein said at least one diphosphonate or methylenephosphonate salt, or acid thereof, is selected from 1-hydroxyethylidene-1,1-diphosphonic acid, or its corresponding tetrasodium salt.

37. The process of claim 31, wherein said at least one diphosphonate or methylenephosphonate salt, or acid thereof, is selected from hexamethylenediaminetetra (methylenephosphonic acid), or its corresponding hexapotassium salt.

38. The process of claim 36, wherein said at least one diphosphonate or methylenephosphonate salt, or acid derivative thereof, is selected from aminotri (methylenephosphonic acid), or its corresponding pentasodium salt.

39. The process of claim 36, wherein said at least one diphosphonate or methylenephosphonate salt, or acid derivative thereof, is selected from diethylenetriaminepenta (methylenephosphonic acid), or its corresponding hexasodium salt.

40. A stabilized hydroxylammonium nitrate-, hydroxylammonium nitrate derivative-, or hydroxylamine-containing composition comprising said hydroxylammonium nitrate, hydroxylammonium nitrate derivative or hydroxylamine and a stabilizing effective amount of a stabilizer mixture consisting of synergistic effective stabilizing amounts of (a) at least one pyridine salt, or an acid derivative thereof; and (b) at least one diphosphonate or methylenephosphonate salt, or acid derivative thereof.

41. The composition of claim 40, wherein said stabilizer mixture is present in said composition in an amount of between approximately 0.0001% wt. to 2% wt.

42. The composition of claim 40, wherein said at least one pyridine salt, or acid thereof, is present in said composition in an amount between approximately 10 to approximately 1,000 parts per million; and wherein said at least one diphosphonate or methylenephosphonate salt, or acid thereof, is present in said composition in an amount of between approximately 10 to approximately 3,000 parts per million.

43. The composition of claim 40, wherein said pyridine or pyridone salt is the sodium salt of 2-hydroxypyridine-N-oxide.

44. The composition of claim 40, wherein said at least one diphosphonate or methylenephosphonate salt, or acid derivative thereof is selected from 1-hydroxyethylidene-1,1iphosphonic acid or its corresponding tetrasodium salt.

45. The composition of claim 40, wherein said at least one diphosphonate or methylenephosphonate salt, or acid derivative thereof is selected from hexamethylenediaminetetra(methylenephosphonic acid), or its corresponding hexapotassium salt.

46. The composition of claim 40, wherein said stabilizer mixture consists of synergistic effective stabilizing amounts of the sodium salt of 2-hydroxypyridine-N-oxide, 1-hydroxyethylidine-1,1-diphosphonic acid and the tetrasodium salt of 1-hydroxyethylidene-1,1-diphosphonic acid.

47. The composition of claim 40, wherein said stabilizer mixture comprises synergistic effective stabilizing amounts of the sodium salt of 2-hydroxypyridine-N-oxide, hexamethylenediaminetetra(methylenephosphonic acid) and the hexapotassium salt of hexamethylenediaminetetra (methylenephosphonic acid).

48. A process for stabilizing hydroxylammonium nitrate, a hydroxylammonium nitrate derivative, or hydroxylamine or a composition consisting of hydroxylammonium nitrate, a hydroxylammonium nitrate derivative or hydroxylamine against unwanted decomposition, which comprises adding to said hydroxylammonium nitrate, hydroxylammonium nitrate derivative or hydroxylamine or compositions consisting of hydroxylammonium nitrate, a hydroxylammonium nitrate derivative or hydroxylamine a stabilizing effective amount of a stabilizer mixture consisting of synergistic effective stabilizing amounts of (a) at least one pyridine salt, or an acid derivative thereof; and (b) at least one diphosphonate or methylenephosphonate salt, or acid thereof to provide a storage stable composition.

49. The process of claim 48, wherein said stabilizer mixture is present in said storage stable composition in an amount of between approximately 0.0001% wt. to 2% wt.

50. The process of claim 48, wherein said at least one pyridine salt, or acid thereof, is present in said storage stable composition in an amount between approximately 10 to approximately 1,000 parts per million; and wherein said at least one diphosphonate or methylenephosphonate salt, or acid derivative thereof, is present in said storage stable composition in an amount of between approximately 10 to approximately 3,000 parts per million.

51. The process of claim 48, wherein said pyridine salt is the sodium salt of 2-hydroxypyridine-N-oxide.

52. The process of claim 48, wherein said at least one diphosphonate or methylenephosphonate salt, or acid derivative thereof is selected from 1-hydroxyethylidene-1,1-diphosphonic acid or its corresponding tetrasodium salt.

53. The process of claim 48, wherein said at least one diphosphonate or methylenephosphonate salt, or acid thereof is selected from hexamethylenediaminetetra(methylenephosphonic acid), or its corresponding hexapotassium salt.

54. The process of claim 48, wherein said stabilizer mixture comprises synergistic effective stabilizing amounts of the sodium salt of 2-hydroxypyridine-N-oxide; 1-hydroxyethylidine-1,1-diphosphonic acid and the tetrasodium salt of 1-hydroxyethylidene-1,1-diphosphonic acid.

55. The process of claim 48, wherein said stabilizer mixture comprises synergistic effective stabilizing amounts of the sodium salt of 2-hydroxypyridine-N-oxide; hexamethylenediaminetetra(methylenephosphonic acid) and the hexapotassium salt of hexamethylenediaminetetra(methylenephosphonic acid).

56. A stabilizer composition for stabilizing hydroxylammonium nitrate, hydroxylammonium nitrate derivatives or hydroxylamine or a composition comprising hydroxylammonium nitrate, a hydroxylammonium nitrate derivative or hydroxylamine consisting of a synergistic effective stabilizing amounts of (a) at least one pyridine salt, or an acid derivative thereof; and (b) at least one diphosphonate or methylenephosphonate salt, or acid derivative thereof.

57. The composition of claim 56, wherein said pyridine salt is the sodium salt of 2-hydroxypyridine-N-oxide.

58. The composition of claim 56, wherein said at least one diphosphonate or methylenephosphonate salt, or acid derivative thereof is selected from 1-hydroxyethylidene-1,1-diphosphonic acid or its corresponding tetrasodium salt.

59. The composition of claim 56, wherein said at least one diphosphonate or methylenephosphonate salt, or acid thereof is selected from hexamethylenediaminetetra(methylenephosphonic acid), or its corresponding hexapotassium salt.

60. The stabilizer composition of claim 56, wherein said stabilizer composition comprises the sodium salt of 2-hydroxypyridine-N-oxide; 1-hydroxyethylidine-1,1-diphosphonic acid and the tetrasodium salt of 1-hydroxyethylidene-1,1-diphosphonic acid.

61. The stabilizer composition of claim 56, wherein said stabilizer composition consists of the sodium salt of 2-hydroxypyridine-N-oxide, hexamethylenediaminetetra(methylenephosphonic acid) and the hexapotassium salt of hexamethylenediaminetetra(methylenephosphonic acid).

* * * * *